United States Patent
Le Guern et al.

(10) Patent No.: US 8,420,644 B2
(45) Date of Patent: Apr. 16, 2013

(54) PHARMACEUTICAL COMPOSITION INTENDED FOR THE PREVENTION OR FOR THE TREATMENT OF CEREBRAL OEDEMAS

(75) Inventors: Marie-Emmanuelle Le Guern, Compiegne (FR); Philippe Girard, Margny-les-Compiegne (FR); Jean-Marie Gillardin, Jonquieres (FR); Laurence Berthon-Cedille, Ricquebourg (FR); Bernard Hublot, Compiegne (FR)

(73) Assignee: Biocodex, Gentilly (FR)

( * ) Notice: Subject to any disclaimer, the term of this patent is extended or adjusted under 35 U.S.C. 154(b) by 0 days.

(21) Appl. No.: 11/446,256

(22) Filed: Jun. 5, 2006

(65) Prior Publication Data
US 2006/0276472 A1    Dec. 7, 2006

(30) Foreign Application Priority Data
Jun. 6, 2005 (FR) .................... 05 05691

(51) Int. Cl.
*A61K 31/537* (2006.01)
*A61K 31/445* (2006.01)
*A61K 31/4015* (2006.01)

(52) U.S. Cl.
USPC ......... 514/237.5; 514/317; 514/424; 514/425

(58) Field of Classification Search ............ 514/651, 514/647, 657, 43; 544/167
See application file for complete search history.

(56) References Cited

U.S. PATENT DOCUMENTS

| | | | | |
|---|---|---|---|---|
| 4,210,754 A | * | 7/1980 | Burkard et al. | 544/167 |
| 5,204,327 A | * | 4/1993 | Kiyota et al. | 514/12 |
| 5,792,799 A | * | 8/1998 | Sherman-Gold | 514/651 |
| 6,011,019 A | * | 1/2000 | Thomas et al. | 514/43 |
| 6,316,504 B1 | * | 11/2001 | Youdim et al. | 514/657 |
| 2002/0072509 A1 | * | 6/2002 | Stein et al. | 514/169 |

OTHER PUBLICATIONS

Priest, "Moclobemide: a range of opportunities." Psychopharmacology 1992: 106;S140-S141.*
Koch et al., "NMDA-antagonism (Memantine): An Alternative Pharmacological Therapeutic Principle in Alzheimer's and Vascular Dementia." Current Pharmaceutical Design (Jan. 2004): 10; 253-259.*
Gorgulu et al., "Reduction of Edema and Infarction by Mamntine and MK-801 After Focal Cerebral Ischaemia and reperfusion in Rat." Acta Neurochir (Wien) 2000: 142;1287-1292.*
Toth et al., "1-Oxa-3,8-diazospiro[4.5]decan-2-one derivatives with potent inhibitory effect on neural Ca-uptake and protecting action against TET-induced brain edema and memory and learning deficits." Eur J Med Chem 1997:32;27-38.*
Bonnet et al., "Moclobemide reduces intracellular pH and neuronal activity of CA3 neurons in guinea-pig hippocampal slices—implication for its neuroprotective properties." Neuropharmacology 2000:39;2067-74.*
Database Biosis 'online': Biosciences Information Services, Phila., Pa; Jul. 2000, Weinstock et al. development of a novel neuroprotective drug, (TV3326) for the treatment of Alzheimer's disease, with cholinesterase . . . , Drug Development Research, vol. 50, No. 3-4.

* cited by examiner

*Primary Examiner* — Walter Webb
(74) *Attorney, Agent, or Firm* — B. Aaron Schulman, Esq.; Stites and Harbison, PLLC

(57) ABSTRACT

The present invention relates to the use of at least one compound of formula (I) below:

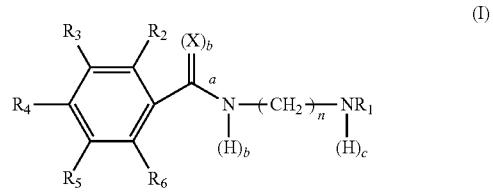

(I)

or at least one of the pharmaceutically acceptable salts thereof, for the preparation of a medicament intended for the prevention or for the treatment of cerebral edemas.

19 Claims, 12 Drawing Sheets

PHARMACEUTICAL COMPOSITION INTENDED FOR THE PREVENTION OR FOR THE TREATMENT OF CEREBRAL OEDEMAS

FIELD OF THE INVENTION

The present invention relates to a pharmaceutical composition intended for the prevention or for the treatment of cerebral edema.

BACKGROUND OF THE INVENTION

Cerebral edema is characterised as being an excessive accumulation of water in the intra- and/or extracellular compartments of the brain (Pollay (1996) In *Neurosurgery*, $2^{nd}$ ed. Mc Graw Hill Book Co., New York, 335-344). Cerebral edema may be of neurological origin, as in the cases of ischaemic attacks, intracerebral haemorrhages, brain tumours, cases of meningitis or of encephalitis, or of non-neurological origin, as in cases of diabetic ketoacidosis, lactic acidosis, hypertensive encephalopathy, malignant hypertension, hyponatraemia or an effect of high altitude.

The principal consequence of cerebral edema is an increase in the intracranial fluid pressure, leading to a reduction in the blood supply to the brain and the partial or total destruction of insufficiently vascularized cerebral tissues.

Few compounds are available for the pharmacological treatment of cerebral edemas, and among the most commonly used the following compounds may be mentioned:

- mannitol, and to a lesser degree glycerol, are used as agents for osmotherapy; however, prolonged administration of mannitol leads to an electrolytic imbalance which can counterbalance its beneficial effects by causing for example cardiopulmonary troubles (Davis et al. (1994) *J. Neurosci. Nurs.* 26:170-174);
- diuretics, such as furosemide, are only used in controlled release to prolong the effect of the osmotic agents;
- corticoids, particularly glucocorticoids, such as dexamethasone, act principally on the blood vessels and are therefore particularly indicated in the case of cerebral edemas of vascular origin; on the other hand they are nor recommended in the treatment of edemas following ischaemias or haemorrhages; moreover, systemic complications associated with steroids can lead to a deterioration of the patient's condition (Rosenberg (2000) In *Neurology in clinical practice*, $3^{rd}$ ed. Butterworth Heinmann, Boston, 2:1545-1559);
- barbiturates, less used than in the past, seem to act by causing a decrease in the level of metabolic activity; however, these compounds also cause systemic hypotension and pulmonary insufficiencies.

Moclobemide is a benzamide derivative which inhibits type A monoamine oxidase in a reversible manner and which is currently used as an antidepressant. Few undesirable side effects following its use are documented.

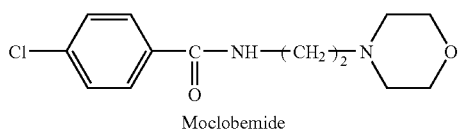

Moclobemide

The synthesis of this compound and of certain of its derivatives is described in the U.S. Pat. No. 4,210,754. Moreover, numerous metabolites of moclobemide have been identified (Jauch et al. (1990) *Acta Psychiatr. Sand. Suppl.* 360:87-90); these metabolites are characterised in particular by a hydroxylation of the phenyl group or by C or N oxidations of the morpholine group.

SUMMARY OF THE INVENTION

The object of the present invention is to provide novel compounds which do not have the drawbacks of the compounds which are already known, within the framework of the prevention or of the treatment of cerebral edema.

In order to achieve this, the present invention derives from the discovery by the inventors that moclobemide allows the prevention or the treatment of cerebral edema.

Therefore the present invention relates to the use of at least one compound of formula (I) below:

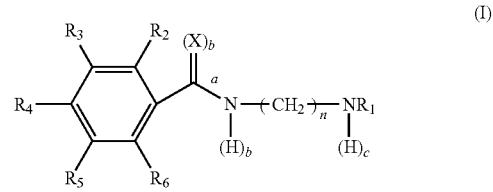

in which:
- n represents a whole number from 1 to 3, and the alkyl chain —$(CH_2)_n$— can be linear or branched,
- X represents O or S
- a represents a single or double bond and b represents 0 or 1, with the proviso that when b represents 0 then a represents a double bond and that when b represents 1 then a represents a single bond;
- c represents 0 or 1;
- $NR_1$ represents an NH group or a heterocycle with 5 or 6 atoms comprising 1 or 2 heteroatoms, selected in particular from O and N, the said heterocycle being possibly substituted by at least one hydroxyl or oxide group, with the proviso that when $NR_1$ represents NH then c represents 1 and that when $NR_1$ represents a heterocycle then c represents 0;
- $R_2$, $R_3$, $R_4$, $R_5$ and $R_6$, which may be identical or different, represent a group selected from the list comprising a hydrogen atom, a halogen atom, in particular selected from F, Cl, Br and I, a hydroxyl group, a linear or branched alkyl group with 1 to 4 carbon atoms, a trifluoromethyl group or a nitro group;

or of a pharmaceutically acceptable salt thereof, for the preparation of a medicament intended for the prevention or for the treatment of cerebral edemas.

DETAILED DESCRIPTION OF THE PREFERRED EMBODIMENTS

The term "cerebral edemas" is used to denote the conditions in which there is an excessive accumulation of water in the intra- and/or extracellular compartments of the brain. Cerebral edemas are described in particular in Pollay (1996) In *Neurosurgery*, $2^{nd}$ ed. Mc Graw Hill Book Co., New York, 335-344.

The synthesis of the above compounds is described in the U.S. Pat. No. 4,210,754, or can be easily deduced by the person skilled in the art on the basis of this same document.

It is possible to verify the activity of prevention or of treatment of cerebral edema of the compounds of formula (I) above, for example in an animal model, such as the rat, by measuring, after sacrifice, the significant decrease in the percentage of water in the brain of animals which have received triethyltin and have been treated with the compounds of formula (I), by comparison with animals which have received triethyltin and not been treated. This test, described by Linee et al., 1984 *Ann. Pharm. Fr.* 42, 431-442, is carried out in the examples.

Advantageously, the compounds of formula (I) above are capable of acting, in particular by inhibiting type A monoamine oxidase, according to a process different from that implemented by the compounds usually used within the framework of the treatment of cerebral edema and therefore do not have their detrimental effects.

In a particular embodiment of the use as defined above of a compound of formula (I), $NR_1$ represents a heterocycle selected from the list comprising:

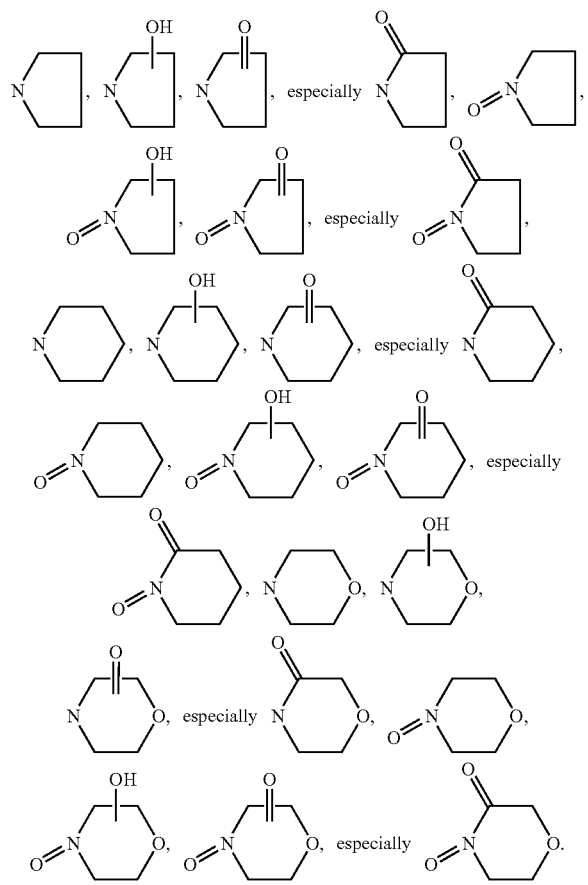

In another particular embodiment of the use as defined above of a compound of formula (I), b represents 1 and X represents O.

In another particular embodiment of the use as defined above of a compound of formula (I), n=2 and the alkyl chain $—(CH_2)_n—$ is not substituted.

In a preferred embodiment the invention also relates to the use as defined above of a compound of formula (I) represented by the following formula (II):

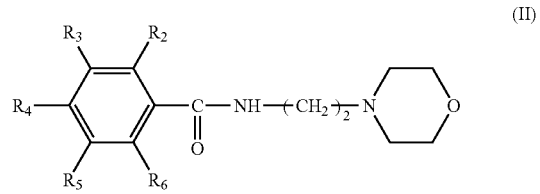

in which $R_2$, $R_3$, $R_4$, $R_5$ and $R_6$ are as defined above, with the proviso that at least one of $R_2$, $R_3$, $R_4$, $R_5$ and $R_6$ represents a halogen atom.

In another preferred embodiment the invention also relates to the use as defined above of a compound of formula (I) represented by moclobemide, of the following formula (III):

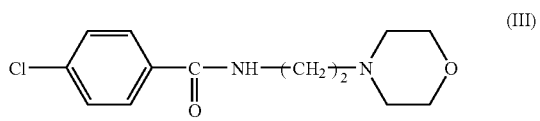

According to a particular embodiment of the use as defined above, the cerebral edema is following a cerebral vascular accident, a cerebral trauma, a cerebral tumour, cerebral metastases of a cancer, a cerebral abscess, a hypertensive attack, a diabetic ketoacidosis or a neuropaludism.

According to a preferred embodiment of the use as defined above, the medicament is suitable for administration to an individual requiring a unitary dose thereof of approximately 5 mg to approximately 900 mg, in particular approximately 150 mg to approximately 450 mg of the compound of formula (I).

According to another preferred embodiment of the use as defined above, the medicament is suitable for administration to an individual requiring a dose thereof of approximately 5 mg/day to approximately 900 mg/day, in particular approximately 150 mg/day to approximately 450 mg/day of the compound of formula (I).

According to another preferred embodiment of the use as defined above, the medicament is suitable for oral, intravenous, intramuscular or rectal administration.

According to yet another preferred embodiment of the use as defined above, the medicament is presented in the form of tablets, capsules, powder, sachets, suppositories, sugar-coated pills, syrups, suspensions or solutions.

In another particular embodiment of the use as defined above, the compound of formula (I) is associated with at least one additional compound intended for the prevention or for the treatment of cerebral edema, such as a compound selected from the list comprising a corticoid, in particular a glucocorticoid, glycerol, mannitol, a diuretic, in particular furosemide, a barbiturate, tetracosactide, an antibiotic, CDP-choline (cytidine 5'-diphosphocholine), vinpocetine, a calcium inhibitor and an NMDA (N-methyl-D-aspartate) antagonist.

Advantageously, the association of a compound of formula (I) with an additional compound indicated in the treatment of cerebral edema makes it possible to reduce the dose or the duration of administration of the said additional compound and thus to limit the side effects thereof.

The present invention also relates to a pharmaceutical composition comprising by way of active substance at least one compound of formula (I) as defined above, or a pharmaceutically acceptable salt thereof, and at least one additional compound intended for the prevention or for the treatment of cerebral edema, such as a compound selected from the list comprising a corticoid, in particular a glucocorticoid, glycerol, mannitol, a diuretic, in particular furosemide, a barbiturate, tetracosactide, an antibiotic, CDP-choline, vinpocetine, a calcium inhibitor, an NMDA antagonist, in association with a pharmaceutically acceptable vehicle.

The present invention also relates to products containing:
at least one compound of formula (I) as defined above, or a pharmaceutically acceptable salt thereof, and
at least one additional compound intended for the prevention or for the treatment of cerebral edema, such as a compound selected from the list comprising a corticoid, in particular a glucocorticoid, glycerol, mannitol, a diuretic, in particular furosemide, a barbiturate, tetracosactide, an antibiotic, CDP-choline, vinpocetine, a calcium inhibitor, and an NMDA antagonist,
as a combined preparation for simultaneous, separate or sequential use for the prevention or the treatment cerebral edema.

DESCRIPTION OF THE DRAWINGS

FIGS. 1A and 1B show the effect of moclobemide (Moc) on the cerebral edema induced by triethyltin (TET) in the rat, measured by the percentage of water in the brain (y axis). The rats are distributed in groups of 10 individuals and are treated over 5 days (from day 0 to day 4).

FIG. 1A: the rats receive neither TET nor moclobemide (−; −), TET in the absence of moclobemide (+; −), moclobemide at the rate of 50 mg/kg 2 times per day in the absence of TET (−; +), or TET (3 mg/kg/day) in the presence of moclobemide at the rate of 50 mg/kg 2 times per day (+; +).

FIG. 1B: the rats receive neither TET nor moclobemide (−; −), TET in the absence of moclobemide (+; −), moclobemide at the rate of 100 mg/kg 2 times per day in the absence of TET (−; +) or TET (3 mg/kg/day) in the presence of moclobemide at the rate of 100 mg/kg 2 times per day (+; +).

The star symbol (*) shows a significant difference with respect to the groups without treatment ($p<0.05$, ANOVA).

FIG. 2A, FIG. 2B

Figure 2A:
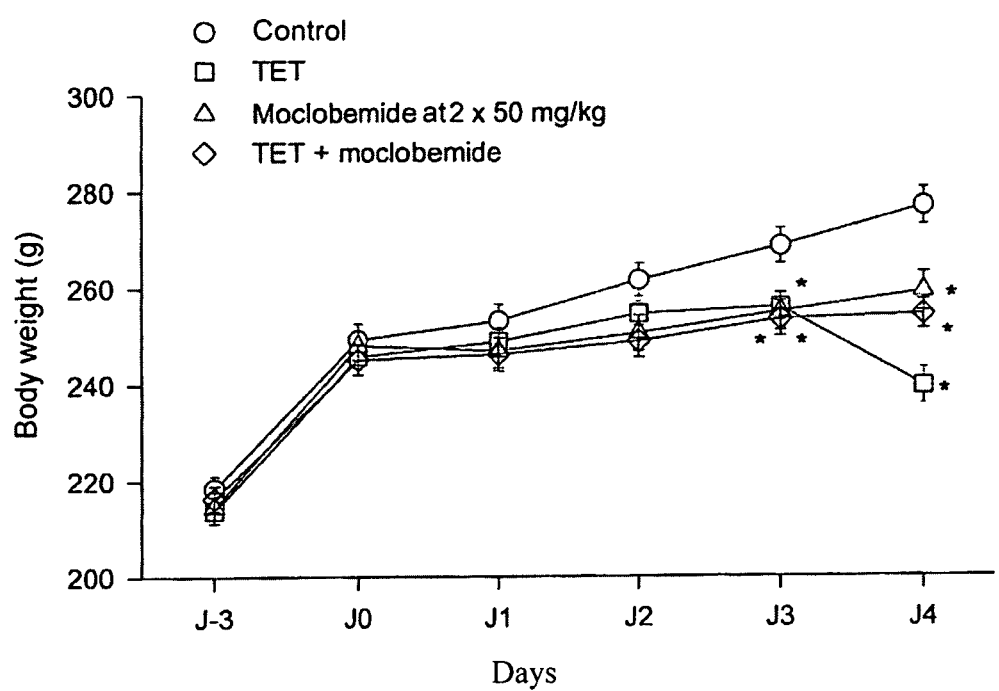
Figure 2B:
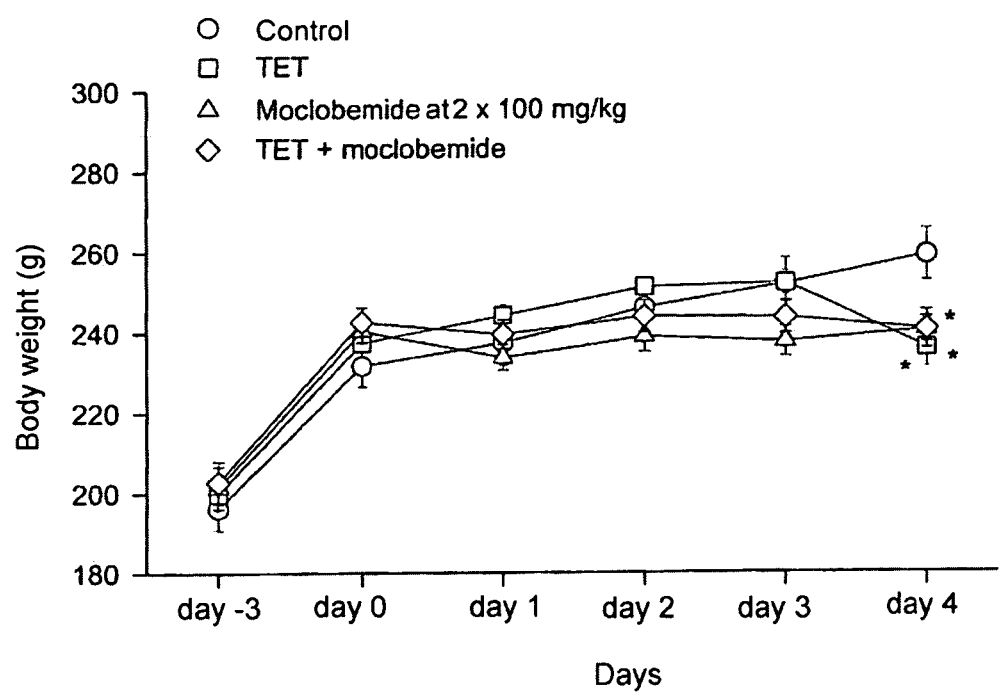

FIGS. 2A and 2B show the effect of moclobemide on the development of the body weight disrupted by triethyltin in the rat (y axis, in grams) as a function of time (x axis, in days). The rats are distributed in groups of 10 individuals and are treated over 5 days (from day 0 to day 4).

FIG. 2A: the rats receive neither TET nor moclobemide (circles), TET in the absence of moclobemide (squares), moclobemide at the rate of 50 mg/kg 2 times per day in the absence of TET (triangles), or TET (3 mg/kg/day) in the presence of moclobemide at the rate of 50 mg/kg 2 times per day (diamonds).

FIG. 2B: the rats receive neither TET nor moclobemide (circles), TET in the absence of moclobemide (squares), moclobemide at the rate of 100 mg/kg 2 times per day in the absence of TET (triangles) or TET (3 mg/kg/day) in the presence of moclobemide at the rate of 100 mg/kg 2 times per day (diamonds).

The star symbol (*) represents a significant difference with respect the respective control groups ($p<0.05$, ANOVA).

FIG. 3A, FIG. 3B

Figure 3A:
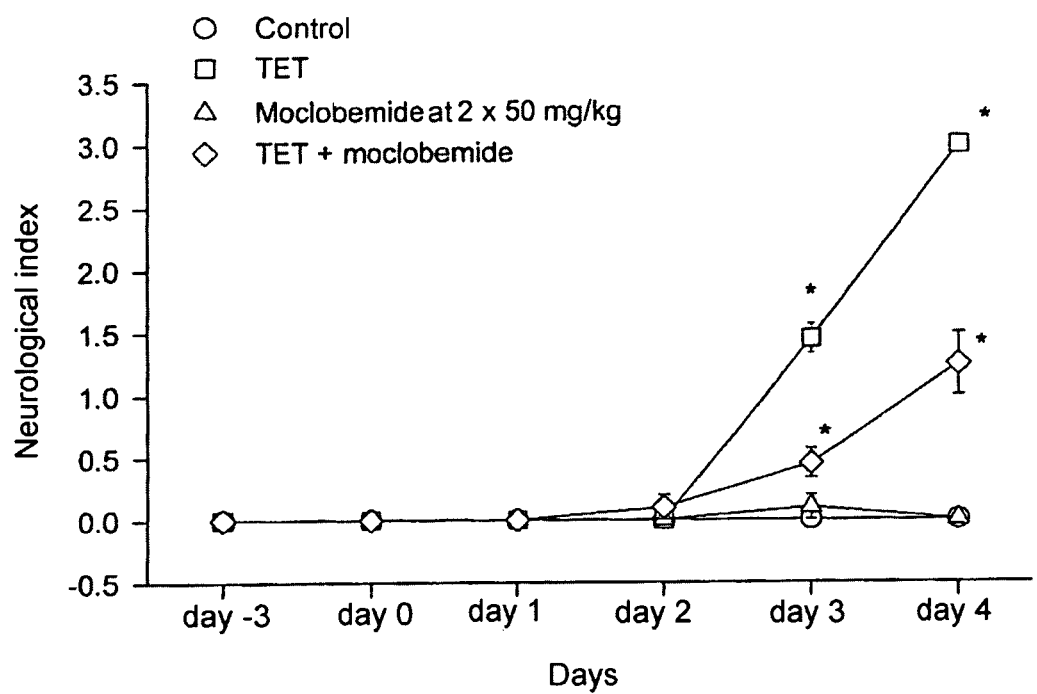
Figure 3B:
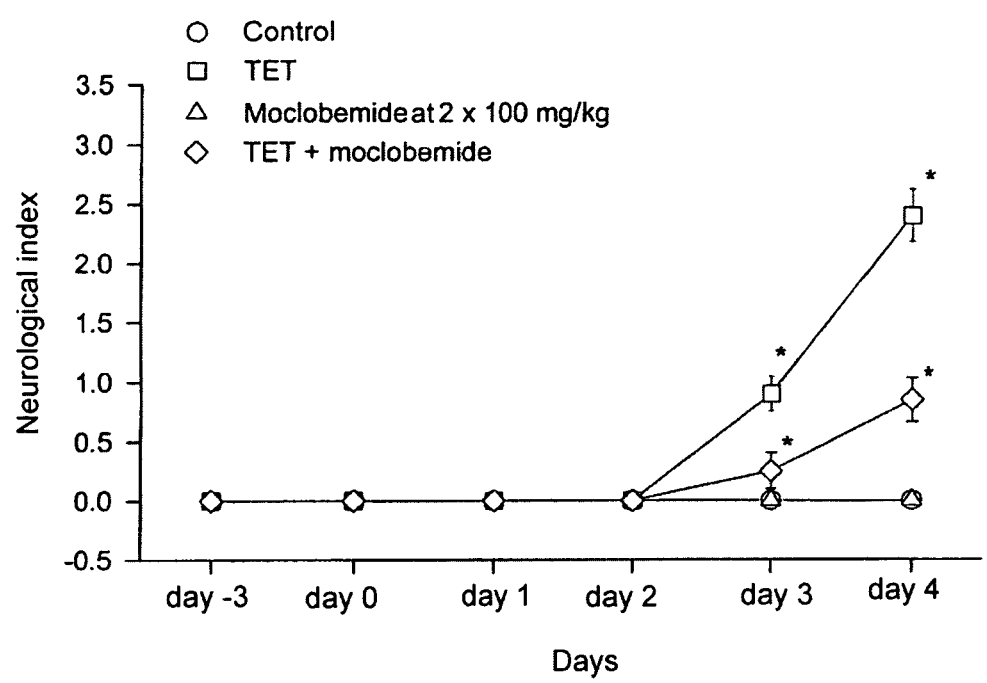

FIGS. 3A and 3B show the effect of moclobemide on the neurological index disrupted by triethyltin in the rat (y axis) as a function of time (x axis, in days). The rats are distributed in groups of 10 individuals and are treated over 5 days (from day 0 to day 4).

FIG. 3A: the rats receive neither TET nor moclobemide (circles), TET in the absence of moclobemide (squares), moclobemide at the rate of 50 mg/kg 2 times per day in the absence of TET (triangles), or TET (3 mg/kg/day) in the presence of moclobemide at the rate of 50 mg/kg 2 times per day (diamonds).

FIG. 3B: the rats receive neither TET nor moclobemide (circles), TET in the absence of moclobemide (squares), moclobemide at the rate of 100 mg/kg 2 times per day in the absence of TET (triangles) or TET (3 mg/kg/day) in the presence of moclobemide at the rate of 100 mg/kg 2 times per day (diamonds).

The star symbol (*) represents a significant difference with respect to the respective control groups ($p<0.05$, ANOVA).

FIG. 4A, FIG. 4B, FIG. 4C

Figure 4A:
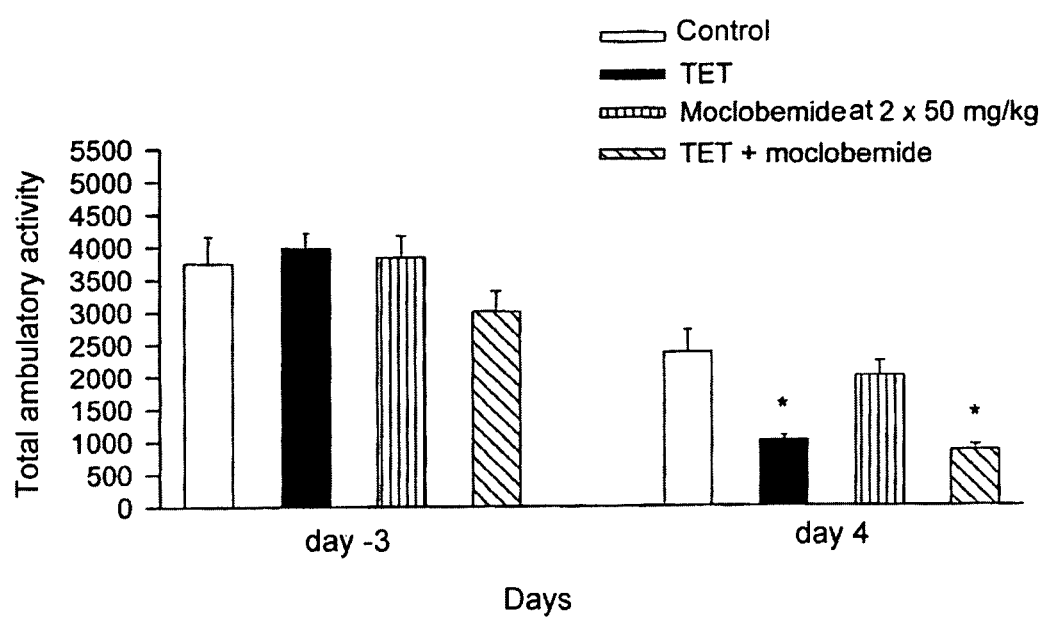
Figure 4B:
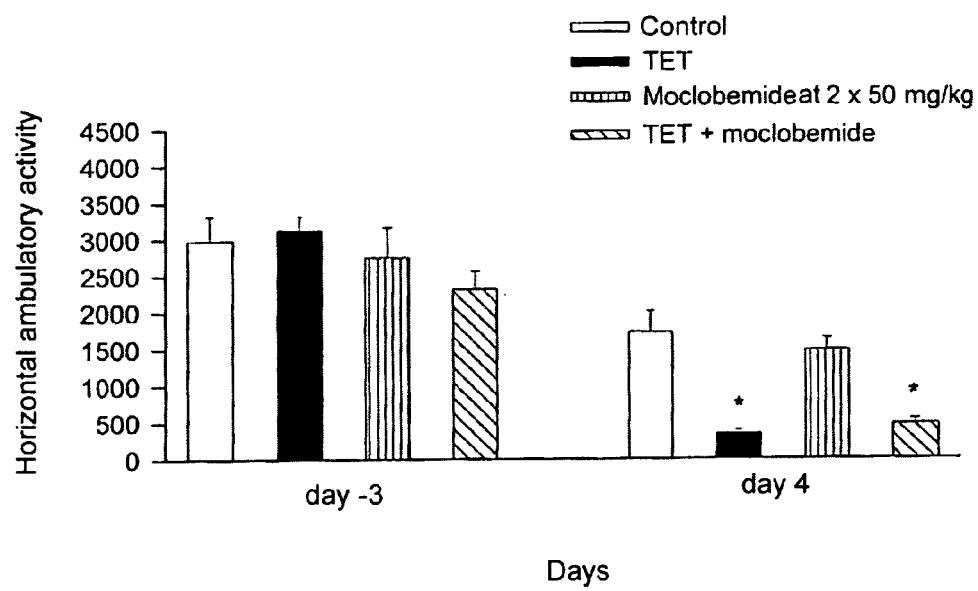
Figure 4C:
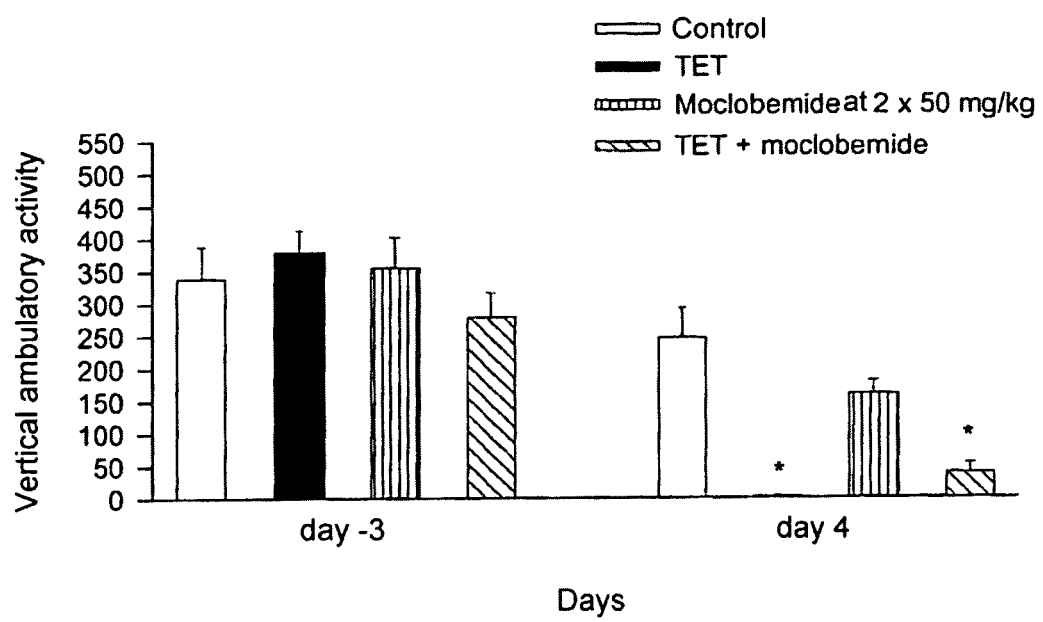

FIGS. 4A, 4B and 4C show respectively the effect of moclobemide on the total (FIG. 4A), horizontal (FIG. 4B) or vertical (FIG. 4C) ambulatory activity (y axis, arbitrary units) disrupted by triethyltin in the rat, three days before any treatment (day −3) or 5 days after the start of the treatment (day 4). The rats are distributed in groups of 10 individuals and are treated over 5 days (from day 0 to day 4).

The rats receive neither TET nor moclobemide (white column), TET in the absence of moclobemide (black column), moclobemide at the rate of 50 mg/kg 2 times per day in the absence of TET (vertically hatched column), or TET (3 mg/kg/day) in the presence of moclobemide at the rate of 50 mg/kg 2 times per day (diagonally hatched column). The star symbol (*) represents a significant difference with respect to the respective control groups ($p<0.05$, ANOVA).

FIG. 5A, FIG. 5B, FIG. 5C

Figure 5A:
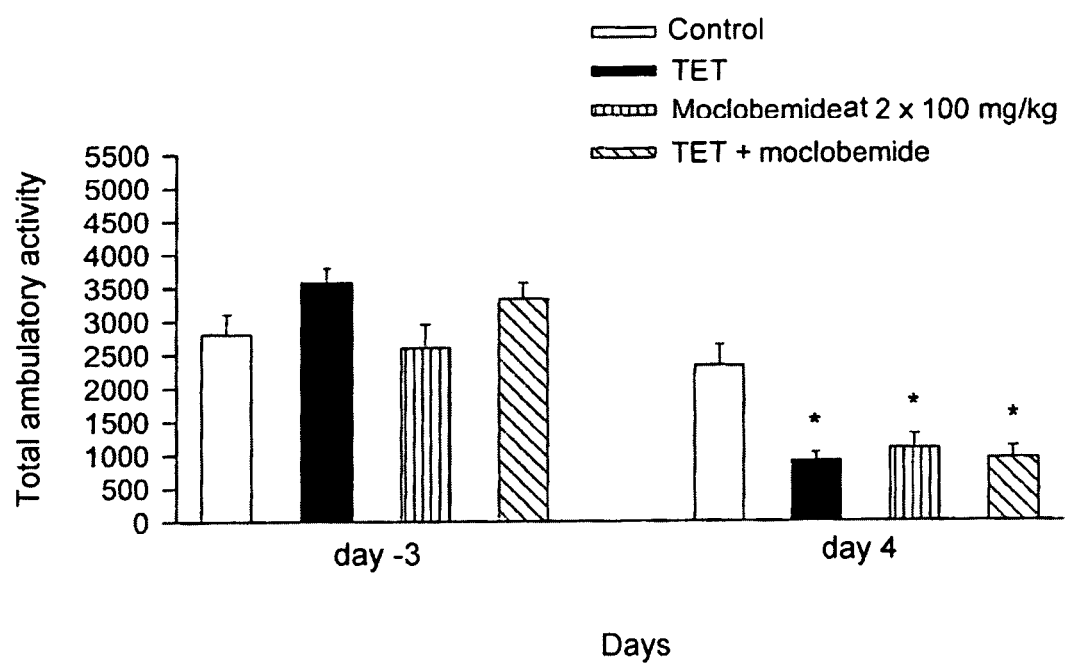
Figure 5B:
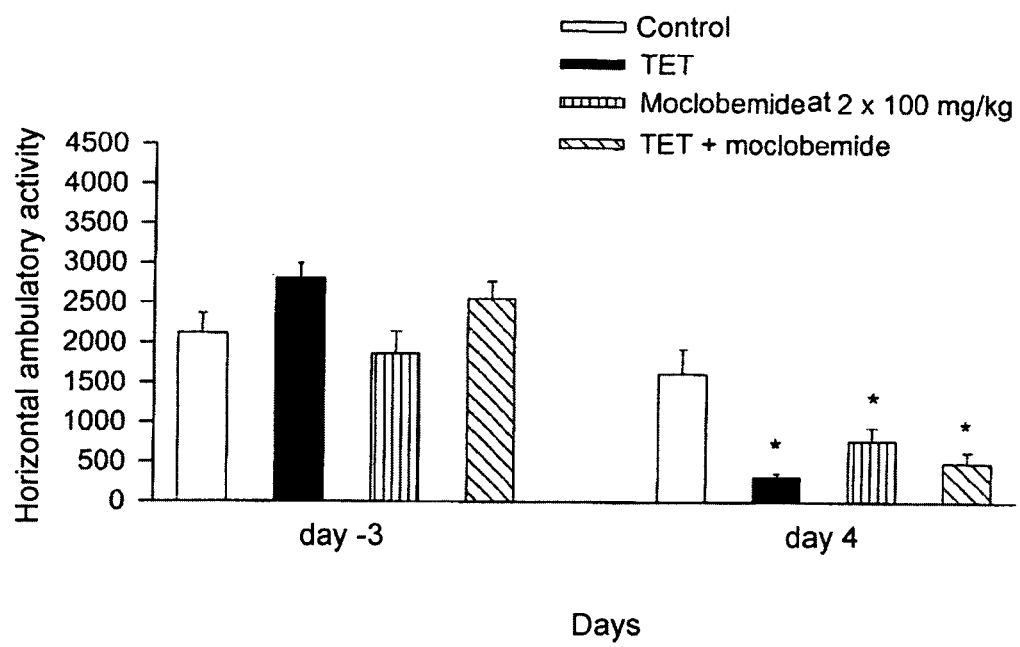
Figure 5C:
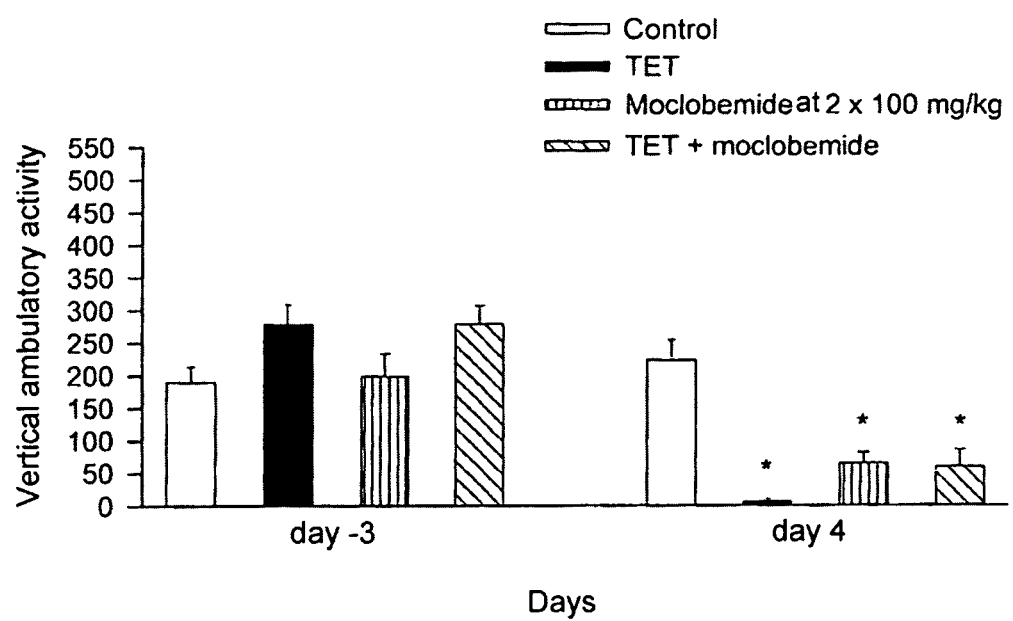

FIGS. 5A, 5B and 5C show respectively the effect of moclobemide on the total (FIG. 5A), horizontal (FIG. 5B) or vertical (FIG. 5C) ambulatory activity (y axis, arbitrary units) disrupted by triethyltin in the rat, three days before any treatment (day −3) or 5 days after the start of the treatment (day 4). The rats are distributed in groups of 10 individuals and are treated over 5 days (from day 0 to day 4).

The rats receive neither TET nor moclobemide (white column), TET in the absence of moclobemide (black column), moclobemide at the rate of 100 mg/kg 2 times per day in the absence of TET (vertically hatched column), or TET (3 mg/kg/day) in the presence of moclobemide at the rate of 100 mg/kg 2 times per day (diagonally hatched column).

The star symbol (*) represents a significant difference with respect to the respective control groups ($p<0.05$, ANOVA).

EXAMPLE

The inventors have demonstrated a protection of the moclobemide on cerebral edema induced by triethyltin (TET) chloride. Moreover, the effect of moclobemide has also been studied on the disruptions induced by TET for the 3 following parameters: weight development, neurological index and ambulatory activity.

1. Material and Methods 1.1. Model

Cerebral edema induced triethyltin (TET) chloride in the rat is a physiopathological model for the study of substances recommended in the treatment of certain cerebrovascular ailments (Linee et al., 1984 *Ann. Pharm. Fr.* 42, 431-442). Intoxication with TET is also a useful toxicological tool for testing products which act at the cerebral level in the elderly person for testing new products in senescence (Bentue-Ferer et al., 1985 *Exp. Aging Res.* 11, 137-141)

Cerebral edema due to TET is a chronic edema, appearing progressively and spontaneously reversible on condition that the intoxication is stopped. This edema develops exclusively at the level of the brain and of the spinal cord. Cerebral edema is characterised by an increase in the contents of water, sodium and chlorides without significant modification of the potassium content. The edema is reflected in a specific attack on the white matter (Naruse et al., 1982 *J. Neurosurg.* 56, 747-752), with a widening of the intramyelinic spaces and attack on the myelin (Kirschner and Sapirstein, 1982 *J. Neurocytol.* 11, 559-569). The myelin of the central nervous system has the potential to recover its integrity after edematous damage by the withdrawal of the accumulated fluid (Yanagisawa et al., 1990 *Neurochem. Res.* 15, 483-486). The scale of the edema, which is accompanied by a weight loss and peripheral neurological disorders, is proportional to the dose of TET.

It has been demonstrated in particular that:

The administration of TET (bromide) at 1 mg/kg/day intraperitoneally for 7 days in the rat increases the percentage of water in the white matter (from 78 to 82%), but not in the grey matter (Naruse et al., 1982 *J. Neurosurg.* 56, 747-752);

The administration of TET (hydrochloride) in drinking water at 2-3%, for 15 days in the rat, increases the percentage of water from 78.0 to 80.0% (Borzeix and Cahn, 1984 *Int. J. Clin. Pharmacol. Res.* 4, 259-261);

The administration of TET (chloride) at 2 mg/kg/day orally for 5 days in the rat increases the percentage of water from 76-77 to 79-80% (Linee et al., 1984 *Ann. Pharm. Fr.* 42, 431-442)

The administration of TET (chloride) at 0.002% in drinking water for 14 days in the rat increases the percentage of water from 78.3 to 81.1% (Otani et al., 1986 *Acta Neuropathol.* (Berl) 69, 54-65).

According to a preventive protocol, the substances to be tested are administered during the intoxication with tin and their activities are measured after 5 days. Under these conditions, it has been shown that certain cerebrovascular medicaments are active, such as dihydroergotoxin, (−)eburnamonine and vincamine (Linee et al., 1984 *Ann. Pharm. Fr.* 42, 431-442).

1.2. Animals

Male Wistar rats from Janvier weighing between 200 and 250 grams at the start of the experiment, are utilised after at least 7 days of acclimatisation in the animal house (room temperature=22±2° C.; relative humidity=50±20%; nutrition UAR "A04"; nycthemeral cycle (12 h/12 h (7.00 a.m.-7.00 p.m./7.00 p.m.-7.00 a.m.)).

1.3. Experimental Protocol

The protocol was adapted according to Linee et al. (Linee et al., 1984 *Ann. Pharm. Fr.* 42, 431-442):

at day −3, the rats are distributed randomly in cages (5 rats per cage)

triethyltin is administered orally for 5 days (from day 0 to day 4) at about 8.00-8.30 a.m.;

the product studied is given orally 2 times per day for 5 days (from day 0 to day 4) at about 9.00-9.30 a.m. and 4.00 p.m.;

the body weight and the neurological index are noted every day;

the ambulatory activity is measured at day −3, before any treatment, and at day 4, at the end of the study;

at the end of the measurements the rat is sacrificed by decapitation, and its brain is removed; each brain is weighed (fresh weight), then is placed in an oven in order to obtain its dry weight.

1.4. Expression of the Results

Water Content of the Brain

The brain is weighed after removal in order to obtain the fresh weight.

The brain is then placed in a drying oven at constant weight at 90° C. for 72 hours, in order to obtain the dry weight.

Then the percentage of water in each brain is calculated.

Finally each brain is placed in the freezer at −20° C. in order to measure the electrolytes subsequently.

Neurological Index: According to the Following 4 Criteria

0: no apparent anomaly

1: loss of spontaneous activity: the rat does not leave a limited surface in a period of 60 seconds, but it escapes normally if it is stimulated (noise, pinching); it has lost its exploratory activity but retains its motor capacities.

2: loss of gripping reflex when the rat is pushed on the surface.

3: loss of retreat reflex, coma followed in the majority of cases by death.

Ambulatory Activity

The motor activity is detected with the aid of 15 photoelectric cells distributed over the walls of the rectangular compartment (320×290×100 mm) of the Opto-Varimex system from Colombus Instruments U.S.A.

The number of displacements (ambulatory activities, horizontally and vertically) of the animal is counted for 15 minutes. The activity is expressed in arbitrary units: 1 unit corresponds to a passage in front of a photoelectric cell.

1.5. Product

The triethyltin bromide at 97% (Sigma, ref 288047) is diluted in distilled water.

The moclobemide (Biocodex) is placed in suspension in Tween 80 at 1% (0.5 ml/100 g).

1.6. Statistics

The statistical test utilised is the analysis of variance. When the result does not depend upon chance (to 5%), the groups treated which differ from the control group are determined.

2. Results 2.1. Effect of the Dose of Triethyltin

Several doses of TET were studied in order to determine a dose enabling reproducible results to be obtained.

The administration of TET at 2 mg/kg/day orally has little effect at the level of the development of the body weight of the rats, and at the level of neurological index.

The administration of TET at 3 mg/kg/day causes a decrease in the body weight of the rats and signs of neurological toxicity from the $4^{th}$ day, but no mortality.

The administration of TET at 4 mg/kg/day leads to signs of neurological toxicity from the $2^{nd}$ day, and of mortality from the $4^{th}$ day.

Consequently, the dose of 3 mg/kg/day was chosen for the following studies.

2.2. Effect of Moclobemide

Cerebral Edema

Figure 1A:
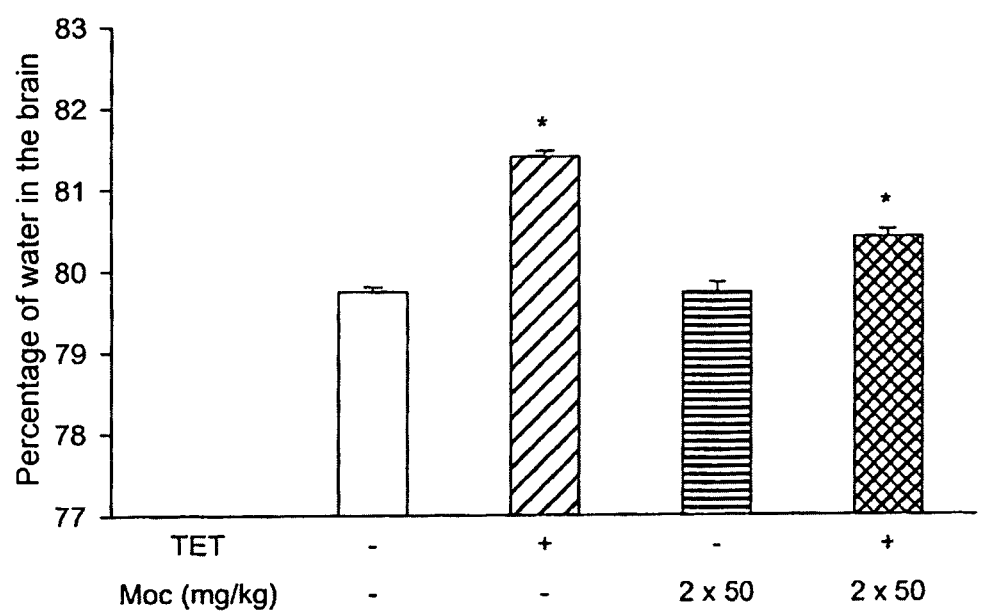
FIG. 1A, FIG. 1B
Figure 1B:
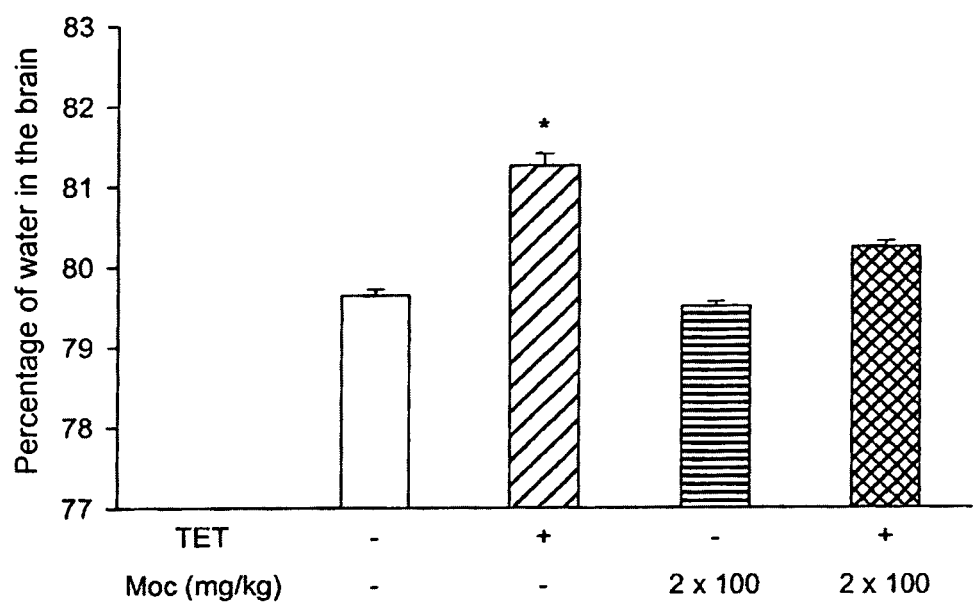

The administration of moclobemide alone at 2×50 or 2×100 mg/kg/day for 5 days does not modify the percentage of water in the brain in the rat (Table 1 and FIGS. 1A, 1B).

TET at 3 mg/kg/day, for 5 days, leads to a significant increase in the percentage of water, from 79.75% and 79.65% respectively for the two control groups, to 81.40% and 81.26% respectively for the two groups treated, indicating the presence of a cerebral edema.

The concomitant administration of moclobemide at 2×50 mg/kg/day and TET does not suppress the significant increase in the percentage of water induced by the TET. On the other hand, at the dose of 2×100 mg/kg/day, the moclobemide inhibits the effect of the TET on the percentage of water.

Body Weight

At the level of the development of the body weight of the rats, TET leads to a significant drop in weight at day 4 (Table 2 and FIGS. 2A, 2B).

Moclobemide administered alone disrupts the weight gain. At the 2 doses utilised, the body weight of the rats is significantly lower at day 4 relative to the control groups.

However, in the presence of TET and of moclobemide at 2×50 mg/kg/day, it is noted that the body weight of the rats at day 4 has not decreased as much as that of the group receiving only TET. In this case, the moclobemide partially prevents the drop in weight induced by the TET.

In the presence of TET and of moclobemide at 2×100 mg/kg/day, it may be noted that the drop in weight observed between day 3 and day 4 in the group receiving only TET is not produced. Therefore moclobemide prevents the drop in weight induced by the TET.

Neurological Index

The administration of moclobemide at 2×50 or 2×100 mg/kg/day for 5 days does not lead to any behavioural sign in the rat (Table 3 and FIG. 3A, 3B).

TET at 3 mg/kg/day, for 5 days, leads to a significant increase in the neurological index from day 3, with a much stronger effect at day 4, indicating substantial neurological troubles.

The concomitant administration of moclobemide at 2×50 mg/kg/day and of TET greatly reduces this neurological index at day 3, and reduces it by half at day 4.

At the dose of 2×100 mg/kg/day, moclobemide also inhibits the effect of TET.

Ambulatory Activity

The administration of moclobemide at 2×50 mg/kg/day for 5 days does not lead to any significant effect on the ambulatory activities in the rat (Table 4 and FIGS. 4A, 4B, 4C).

On the other hand, at the dose of 2×100 mg/kg/day, the administration of moclobemide significantly decreases the ambulatory activities at day 4 (Table 5 and FIGS. 5A, 5B, 5C).

TET at 3 mg/kg/day, for 5 days, leads to a great decrease in the ambulatory activities at day 4, with and almost total inhibition of the vertical ambulatory activity.

The concomitant administration of moclobemide at 2×50 or 2×100 mg/kg/day and of TET does not suppress the effect of TET, but reduces it partially at the level of the vertical ambulatory activity.

TABLE 1

Effect of moclobemide on the cerebral oedema induced by triethyltin (TET) by measuring the percentage of water in the brain, in the rat (n =10). The rat receives, orally over 5 days, moclobemide 2 times per day and TET at 3 mg/kg/day. On the 5$^{th}$ day, the brain is removed then dried for 72 hours at 90° C., in order to determine the percentage of water present in the brain.

| TET (mg/kg/day) | Moclobemide (mg/kg/day) | Percentage of water (mean ± esm) | Variation in percentage | Statistical Test ANOVA |
|---|---|---|---|---|
| 0 | 0 | 79.75 ± 0.06 | | |
| 3 | 0 | 81.40 ± 0.07 | +1.65 | p < 0.05 |
| 0 | 2 × 50 | 79.74 ± 0.12 | −0.01 | Ns |
| 3 | 2 × 50 | 80.42 ± 0.09 | +0.67 | p < 0.05 |
| 0 | 0 | 79.65 ± 0.07 | | |
| 3 | 0 | 81.26 ± 0.15 | 1.61 | p < 0.05 |
| 0 | 2 × 100 | 79.51 ± 0.06 | −0.14 | Ns |
| 3 | 2 × 100 | 80.24 ± 0.08 | +0.59 | Ns |

TABLE 2

Effect of moclobemide on the development of the body weight disrupted by triethyltin (TET) in the rat (n = 10). Starting from day 0, the rat receives orally over 5 days, moclobemide 2 times per day and TET at 3 mg/kg/day. (* : p < 0.05 by an ANOVA statistical test in order to compare the treated groups with the group without treatment).

| TET (mg/kg/day) | Moclobemide (mg/kg/day) | Body weight (grammes ± esm) | | | | | |
|---|---|---|---|---|---|---|---|
| | | day −3 | day 0 | day 1 | day 2 | day 3 | day 4 |
| 0 | 0 | 218± 3 | 249± 3 | 253± 4 | 262± 3 | 269± 4 | 277± 4 |
| 3 | 0 | 214 ± 2 | 246 ± 2 | 249 ± 3 | 255 ± 3 | 256 ± 3* | 240 ± 4* |
| 0 | 2 × 50 | 215 ± 3 | 248 ± 3 | 247 ± 4 | 251 ± 4 | 255 ± 4* | 259 ± 4* |
| 3 | 2 × 50 | 216 ± 3 | 245 ± 3 | 246 ± 3 | 249 ± 3 | 253 ± 4* | 254 ± 3* |
| 0 | 0 | 196 ± 5 | 232 ± 5 | 237 ± 6 | 246 ± 6 | 252 ± 6 | 259 ± 6 |
| 3 | 0 | 200 ± 4 | 237 ± 2 | 244 ± 3 | 251 ± 2 | 252 ± 3 | 236 ± 5* |
| 0 | 2 × 100 | 201 ± 5 | 240 ± 3 | 234 ± 3 | 239 ± 4 | 238 ± 4 | 241 ± 3* |
| 3 | 2 × 100 | 203 ± 5 | 243 ± 4 | 240 ± 3 | 244 ± 4 | 244 ± 4 | 241 ± 5* |

TABLE 3

Effect of moclobemide on the neurological index disrupted by triethyltin (TET) as a function of time, in the rat (n = 10). Starting from day 0, the rat receives orally over 5 days, moclobemide 2 times per day and TET at 3 mg/kg/day. (* : p < 0.05, ANOVA statistical test with respect to the respective control groups).

| TET (mg/kg/day) | Moclobemide (mg/kg/day) | day −3 | day 0 | day 1 | day 2 | day 3 | day 4 |
|---|---|---|---|---|---|---|---|
| 0 | 0 | 0 | 0 | 0 | 0 | 0 | 0 |
| 3 | 0 | 0 | 0 | 0 | 0 | 1.45 ± 0.12* | 3* |
| 0 | 2 × 50 | 0 | 0 | 0 | 0 | 0.10 ± 0.10 | 0 |
| 3 | 2 × 50 | 0 | 0 | 0 | 0.10 ± 0.10 | 0.45 ± 0.12* | 1.25 ± 0.25* |
| 0 | 0 | 0 | 0 | 0 | 0 | 0 | 0 |
| 3 | 0 | 0 | 0 | 0 | 0 | 0.90 ± 0.15* | 2.40 ± 0.22* |
| 0 | 2 × 100 | 0 | 0 | 0 | 0 | 0 | 0 |
| 3 | 2 × 100 | 0 | 0 | 0 | 0 | 0.25 ± 0.15* | 0.85 ± 0.18* |

Neurological index:
0 → no apparent anomaly
1 → loss of spontaneous activity: the rat does not leave a limited surface in a period of 60 seconds, but it escapes normally if it is stimulated (noise, pinching); it has lost its exploratory activity but retains its motor capacities
2 → loss of the gripping reflex when the rat is pushed on the surface
3 → loss of the retreat reflex, coma followed in the majority of cases by death

TABLE 4

Effect of moclobemide on the ambulatory activity (arbitrary unit) disrupted by triethyltin (TET) in the rat (n = 10). The rat receives orally over 5 days, moclobemide 2 times per day and TET at 3 mg/kg/day. The measurements are carried out at day −3, before any treatment, and at day 4, at the end of the study. ( * : p < 0.05, statistical ANOVA test with respect to the respective control groups).

| TET (mg/kg/day) | Moclobemide (mg/kg/day) | Day −3 (means ± esm) | Day 4 (means ± esm) |
|---|---|---|---|
| TOTAL AMBULATORY ACTIVITY | | | |
| 0 | 0 | 3748 ± 406 | 2372 ± 340 |
| 3 | 0 | 3986 ± 225 | 1005 ± 76* |
| 0 | 2 × 50 | 3840 ± 323 | 2000 ± 224 |
| 3 | 2 × 50 | 3001 ± 314 | 844 ± 88* |
| HORIZONTAL AMBULATORY ACTIVITY | | | |
| 0 | 0 | 2984 ± 333 | 1728 ± 291 |
| 3 | 0 | 3127 ± 195 | 345 ± 45* |
| 0 | 2 × 50 | 2754 ± 415 | 1483 ± 163 |
| 3 | 2 × 50 | 2319 ± 248 | 474 ± 70* |
| VERTICAL AMBULATORY ACTIVITY | | | |
| 0 | 0 | 339 ± 50 | 247 ± 45 |
| 3 | 0 | 379 ± 34 | 2 ± 1* |
| 0 | 2 × 50 | 355 ± 46 | 160 ± 20 |
| 3 | 2 × 50 | 279 ± 37 | 39 ± 14* |

TABLE 5

Effect of moclobemide on the ambulatory activity (arbitrary unit) disrupted by triethyltin (TET) in the rat (n =10). The rat receives orally over 5 days, moclobemide 2 times per day and TET at 3 mg/kg/day. The measurements are carried out at day −3, before any treatment, and at day 4, at the end of of the study. ( * : p < 0.05, ANOVA statistical test with respect to the respective control groups).

| TET (mg/kg/day) | Moclobemide (mg/kg/day) | Day −3 (means ± esm) | Day 4 (means ± esm) |
|---|---|---|---|
| TOTAL AMBULATORY ACTIVITY | | | |
| 0 | 0 | 2804 ± 300 | 2334 ± 309 |
| 3 | 0 | 3580 ± 211 | 906 ± 121* |
| 0 | 2 × 100 | 2599 ± 360 | 1091 ± 218* |
| 3 | 2 × 100 | 3332 ± 235 | 11 945 ± 180* |
| HORIZONTAL AMBULATORY ACTIVITY | | | |
| 0 | 0 | 2118 ± 247 | 1619 ± 306 |
| 3 | 0 | 2807 ± 190 | 322 ± 44* |
| 0 | 2 × 100 | 1863 ± 276 | 776 ± 168* |
| 3 | 2 × 100 | 2549 ± 221 | 497 ± 139* |
| VERTICAL AMBULATORY ACTIVITY | | | |
| 0 | 0 | 189 ± 24 | 223 ± 31 |
| 3 | 0 | 278 ± 30 | 6 ± 4* |
| 0 | 2 × 100 | 199 ± 35 | 64 ± 17* |
| 3 | 2 × 100 | 279 ± 27 | 59 ± 27* |

What is claimed is:

1. A method for treating cerebral edemas in an individual in need thereof, by inhibiting type A monoamine oxidase, comprising administering to said individual a therapeutically effective amount of at least one compound of formula (I) below:

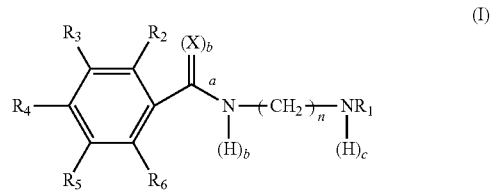

in which:

n represents a whole number from 1 to 3, and the alkyl chain —$(CH_2)_n$— can be linear or branched, X represents O or S;

a represents a single or double bond and b represents 0 or 1, with the proviso that when b represents 0 then a represents a double bond and that when b represents 1 then a represents a single bond;

c represents 0 or 1;

$NR_1$ represents an NH group or a heterocycle with 5 or 6 atoms comprising 1 or 2 heteroatoms, the said heterocycle being possibly substituted by at least one hydroxyl or oxide group, with the proviso that when $NR_1$ represents NH then c represents 1 and that when $NR_1$ represents a heterocycle then c represents 0;

$R_2$, $R_3$, $R_4$, $R_5$ and $R_6$, which may be identical or different, represent a group selected from the list comprising a hydrogen atom, a halogen atom, a hydroxyl group, a linear or branched alkyl group with 1 to 4 carbon atoms, a trifluoromethyl group or a nitro group;

or of a pharmaceutically acceptable salt thereof;

wherein said compounds are capable of inhibiting type A monoamine oxidase.

2. The method according to claim 1, wherein $NR_1$ represents a heterocycle selected from the list consisting of:

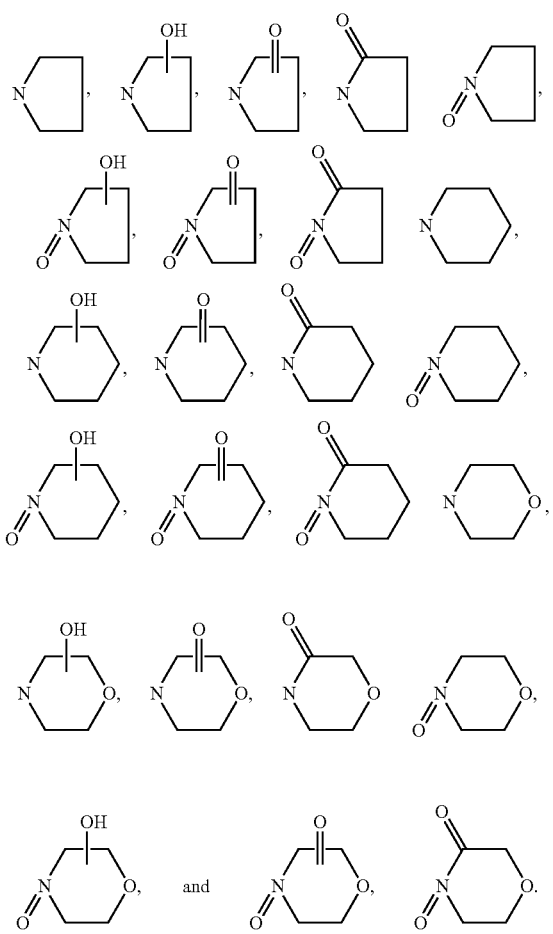

3. The method according to claim 1, wherein b represents 1 and X represents 0.

4. The method according to claim 1, wherein n=2 and the alkyl chain $—(CH_2)_n—$ is not substituted.

5. The method according to claim 1, wherein the compound of formula (I) is represented by the following formula (II):

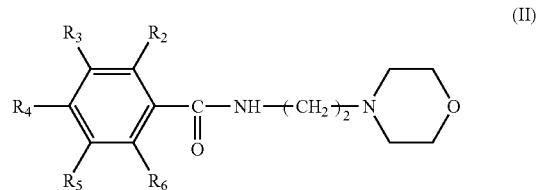

in which $R_2$, $R_3$, $R_4$, $R_5$ and $R_6$ are as defined in claim 1, with the proviso that at least one of $R_2$, $R_3$, $R_4$, $R_5$ and $R_6$ represents a halogen atom.

6. The method according to claim 1, wherein the compound of formula (I) is represented by the moclobemide, of formula (III) below:

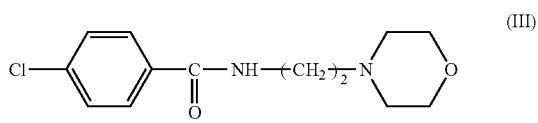

7. The method according to claim 1, wherein the cerebral edema is following a cerebral vascular accident, a cerebral trauma, a cerebral tumour, cerebral metastases of a cancer, a cerebral abscess, a hypertensive attack, a diabetic ketoacidosis or a neuropaludism.

8. The method according to claim 1, wherein the compound of formula (I) is administered at a unitary dose of approximately 5 mg to approximately 900 mg.

9. The method according to claim 1, wherein the compound of formula (I) is administered at a dose of approximately 5 mg/day to approximately 900 mg/day.

10. The method according to claim 1, wherein the compound of formula (I) is administered by the oral, intravenous, intramuscular or rectal route.

11. The method according to claim 1, wherein the compound of formula (I) is administered in the form of tablets, capsules, powder, sachets, suppositories, sugar-coated pills, syrups, suspensions or solutions.

12. The method according to claim 1, wherein the compound of formula (I) is simultaneously, separately or sequentially administered with at least one additional compound intended for the prevention or for the treatment of cerebral edema, such as a compound selected from the list consisting of a corticoid, glycerol, mannitol, a diuretic, a barbiturate, tetracosactide, an antibiotic, CDP-choline, vinpocetine, a calcium inhibitor and an NMDA antagonist.

13. The method according to claim 8, wherein the compound of formula (I) is administered at a unitary dose of approximately 150 mg to approximately 450 mg.

14. The method according to claim 9, wherein the compound of formula (I) is administered at a dose of approximately 150 mg/day to approximately 450 mg/day.

15. The method according to claim 1, wherein the heteroatom is selected from the group consisting of O and N.

16. The method according to claim 1, wherein the halogen atom is selected from the group consisting of F, Cl, Br, and I.

17. The method according to claim 2, wherein NR1 is selected from the group consisting of:
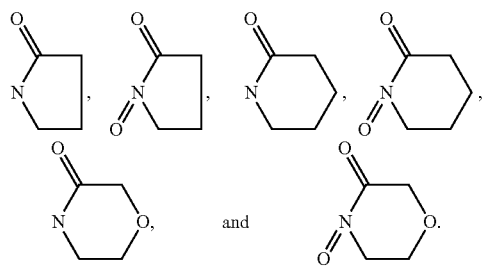
18. The method according to claim 12, wherein the corticoid is a glucocorticoid.
19. The method according to claim 12, wherein the diuretic is furosemide.
* * * * *